(12) United States Patent
Kim et al.

(10) Patent No.: US 12,108,817 B2
(45) Date of Patent: Oct. 8, 2024

(54) COMPRESSION VEST FOR CHILD WITH AUTISM SPECTRUM DISORDER

(71) Applicant: DOLBOMDREAM CO., LTD., Daejeon (KR)

(72) Inventors: Ji Hun Kim, Gyeonggi-do (KR); Dong Yup Han, Daejeon (KR); Cheol Jun Park, Daejeon (KR); Meen Tai Kim, Sejong (KR)

(73) Assignee: DOLBOMDREAM CO., LTD., Daejeon (KR)

( * ) Notice: Subject to any disclaimer, the term of this patent is extended or adjusted under 35 U.S.C. 154(b) by 0 days.

(21) Appl. No.: 18/043,399

(22) PCT Filed: Nov. 26, 2021

(86) PCT No.: PCT/KR2021/017580
§ 371 (c)(1),
(2) Date: Feb. 28, 2023

(87) PCT Pub. No.: WO2022/177108
PCT Pub. Date: Aug. 25, 2022

(65) Prior Publication Data
US 2024/0008566 A1    Jan. 11, 2024

(30) Foreign Application Priority Data

Feb. 19, 2021    (KR) .................. 10-2021-0022273

(51) Int. Cl.
*A41D 13/018*    (2006.01)
*A41D 1/04*    (2006.01)
*A41D 11/00*    (2006.01)

(52) U.S. Cl.
CPC ............. *A41D 13/018* (2013.01); *A41D 1/04* (2013.01); *A41D 11/00* (2013.01)

(58) Field of Classification Search
CPC ...... F41H 1/02; A61F 5/32; A61F 5/05; A61F 5/34; A61M 21/02
(Continued)

(56) References Cited

U.S. PATENT DOCUMENTS

| 2003/0074711 A1* | 4/2003 | Iversen ................ A61H 9/0078 |
| | | 434/236 |
| 2004/0040064 A1* | 3/2004 | Mah ........................ B64G 6/00 |
| | | 2/2.14 |

(Continued)

FOREIGN PATENT DOCUMENTS

| KR | 10-2003-0095723 A | 12/2003 |
| KR | 10-2006-013300 A | 2/2006 |

(Continued)

OTHER PUBLICATIONS

International Search Report for corresponding International Application No. PCT/KR2021/017580 mailed Mar. 2, 2022.

(Continued)

*Primary Examiner* — Jameson D Collier
*Assistant Examiner* — Matthew R Marchewka
(74) *Attorney, Agent, or Firm* — Revolution IP, PLLC (57) ABSTRACT

A compression vest for a child with a Autism Spectrum Disorder has front and rear air tube pads embedded in a front and a rear portions, an air is injected into the front and rear air tube pads embedded in the front and rear portions, the injected air is controlled via an application installed in a mobile terminal, the air is also injected using a manual pump, and the front and rear air tube pads embedded in a front portion and a rear portion of a vest outer skin have a circular bonding portion and a linear bonding portion so that, while the injected air is not allowed to escape to the outside and the air tube pads evenly inflate and apply uniform pressure throughout the vest, an air pressure of the air tube (Continued)

pads is directed inward, and thus pressurization is increased relative to the amount of injected air.

6 Claims, 9 Drawing Sheets

(58) Field of Classification Search
USPC .................................................................. 2/102
See application file for complete search history.

(56) References Cited

U.S. PATENT DOCUMENTS

| | | | | |
|---|---|---|---|---|
| 2008/0153590 | A1* | 6/2008 | Ombrellaro | A63F 13/285 |
| | | | | 463/30 |
| 2008/0249441 | A1* | 10/2008 | Avitable | A61F 13/085 |
| | | | | 601/151 |
| 2010/0325773 | A1* | 12/2010 | Rock | F41H 1/02 |
| | | | | 2/113 |
| 2011/0093003 | A1* | 4/2011 | Lee | A61B 17/1355 |
| | | | | 606/201 |
| 2012/0246788 | A1* | 10/2012 | Harrell | A41D 13/0155 |
| | | | | 2/243.1 |
| 2013/0289455 | A1* | 10/2013 | Clapp | A61H 9/0007 |
| | | | | 601/149 |
| 2016/0001034 | A1 | 1/2016 | Rembrand | |

FOREIGN PATENT DOCUMENTS

| | | |
|---|---|---|
| KR | 10-2006-0034514 A | 4/2006 |
| KR | 20-0446466 A | 10/2009 |
| KR | 10-1246924 B1 | 3/2013 |
| KR | 10-1943793 B1 | 1/2019 |
| KR | 10-2020-0112017 A | 10/2020 |
| KR | 10-2301717 A | 9/2021 |

OTHER PUBLICATIONS

Written Opinion for corresponding International Application No. PCT/KR2021/017580 dated Mar. 2, 2022 and English translation.

* cited by examiner

COMPRESSION VEST FOR CHILD WITH AUTISM SPECTRUM DISORDER

TECHNICAL FIELD

The present disclosure relates to a compression vest for a child with a Autism Spectrum Disorder that has an auxiliary role in stabilizing a child with a Autism Spectrum Disorder to allow efficient progress in therapeutic education, and more particularly, to a compression vest for a child with a Autism Spectrum Disorder that has front and rear air tube pads embedded in a front portion, which is a portion near a chest of a wearer, and a rear portion, which is a portion near a back of the wearer, wherein the front and rear air tube pads embedded in the front and rear portions expand due to air being injected thereinto with a set pressure suitable for stabilizing a child with a Autism Spectrum Disorder, air may be injected with a manual pump while the set pressure with which air is injected into the air tube pads is controlled through an application installed in a mobile terminal, and the front and rear air tube pads embedded in a front portion and a rear portion of a vest outer skin constituting the compression vest for a child with a Autism Spectrum Disorder have a circular bonding portion and a linear bonding portion so that, while the air tube pads evenly inflate due to the injected air and apply uniform pressure throughout the compression vest, an air pressure of the air tube pads is directed inward, and thus pressurization efficiency is increased relative to the amount of injected air.

BACKGROUND ART

Generally, a vest is a short, close-fitting, sleeveless upper garment. Due to being sleeveless, a vest enables the wearer to be active. A vest is a supplementary upper garment that is worn over a top. In some cases, air is injected into a vest to allow the wearer to float in water, or a vest is worn to maintain warmth or mitigate external impact. A vest may be worn to cover body flaws, or a therapeutic vest may be worn to apply pressure to a surgical site, such as the chest, for a therapeutic purpose.

As the related art in which air is injected into a vest to allow the vest to be used for multiple purposes, Korean Utility Model Registration No. 20-0446466 discloses a "Multifunctional vest" in which an air layer is formed inside the vest to improve a warmth maintaining function, allow the wearer to float in water, and protect the wearer from external impact. However, in the multifunctional vest, an air sheet in which an air layer is provided is simply added to the vest, and the vest does not have a function that allows the vest to be controlled by injecting air thereinto.

Also, as the related art in which a predetermined pressure is applied to a vest for a therapeutic purpose, Korean Patent Registration No. 10-1246924 discloses "Clothing for improving attention of children with disabilities" in which a volume varying portion is provided between an outer portion and an inner portion of a vest to adjust pressure stimulation and allow the vest to be utilized in sensory integration therapy for children with attention deficit disorder or children who have difficulty in controlling their senses. The patent includes the volume varying portion whose volume varies due to an inflow and outflow of air and a controller that is able to adjust the volume and internal pressure of the volume varying portion. However, since the volume varying portion is disposed only in a portion of the vest, and pressure of the volume varying portion which inflates as air is injected is not uniformly applied to the vest while the vest is worn by a wearer, there is a limitation in improving attention of the wearer.

In addition, as the related art which is a compression garment for therapy using air injection, Korean Patent Registration No. 10-1943793 discloses an "Air injection type medical pressure garment" which includes a stretchy fabric, a plurality of pockets disposed at one side of the fabric and having a hollow formed therein, a partition configured to divided the hollow between the pockets, an airbag, a pressure sensor, a communicating portion, and the like in order to press a specific body part of the wearer. The pressure garment is configured to press a specific body part and does not include an element that applies uniform pressure to the wearer's upper body, including the back and chest of the wearer, to stabilize the wearer's body.

DISCLOSURE

Technical Problem

The present disclosure is directed to providing a compression vest for a child with a Autism Spectrum Disorder in which an air tube pad is embedded in a front portion, which is a portion near a chest of a wearer, and a rear portion, which is a portion near a back of the wearer, of a vest outer skin constituting the compression vest, and air is injected into the front and rear air tube pads with a predetermined set pressure and pressure maintenance time so that, when the compression vest is worn, a sharp increase of air pressure due to air injection is prevented, and the compression vest can be worn safely.

The present disclosure is also directed to providing a compression vest for a child with a Autism Spectrum Disorder in which a controller, a driving portion, and a sensor portion are included to provide a function that allows an amount of air injected into the air tube pads and an air pressure of the air tube pads to be adjusted according to preferences of a child with a Autism Spectrum Disorder and adjusted to values necessary for therapy.

The present disclosure is also directed to providing a compression vest for a child with a Autism Spectrum Disorder in which unit modules using a linear adhesive portion and a circular adhesive portion to form a path for injected air are formed to be continuously connected on upper, lower, left, and right portions of the air tube pads so that the air tube pads inflate evenly throughout at a predetermined height due to the injected air and apply uniform pressure to the chest and back of the wearer, thus giving a sense of stability to a child with a Autism Spectrum Disorder by letting the child feel as if his or her upper body is being warmly embraced, and increasing a healing effect.

The present disclosure is also directed to providing a compression vest for a child with a Autism Spectrum Disorder in which, in order to induce the air tube pads that inflate due to the air injected into the air tube pads to inflate inward toward the wearer's body, primarily, a thickness of an outer skin of the air tube pads is formed thicker than a thickness of an inner skin of the air tube pads, and secondarily, an inner portion of the vest outer skin is made of a stretchy material and an outer portion of the vest outer skin is made of a non-stretchy material so that an air pressure of the air tube pads is directed inward, and thus pressurization efficiency is increased relative to the amount of injected air.

The present disclosure is also directed to providing a compression vest for a child with a Autism Spectrum Disorder in which, by a connecting portion configured using a hook-and-loop fastener and the like, the front portion and the rear portion constituting the vest outer skin are coupled to each other so that the size of the vest outer skin can be adjusted according to a change in the size of the wearer's upper body, and a function that allows a degree of adhesion of the compression vest to the wearer's body to be adjusted is provided in cooperation with the pressure of the injected air.

The objectives of the present disclosure are not limited to those mentioned above, and other unmentioned objectives should be clearly understood by those of ordinary skill in the art to which the present disclosure pertains from the present specification and the accompanying drawings.

Technical Solution

The present application discloses a compression vest for a child with a Autism Spectrum Disorder, the compression vest including: a vest outer skin that consists of a front portion, which is a portion near a chest of a wearer, and a rear portion, which is a portion near a back of the wearer; an air tube pad embedded in each of the front portion and the rear portion of the vest outer skin; a driving portion configured to inject air into the air tube pads by a controller configured to control the air injected into the air tube pads; a sensor portion configured to check a set pressure and pressure maintenance time of the injected air; circular adhesive portions and linear adhesive portions that are formed on the air tube pads so that the air tube pads inflate evenly throughout at a predetermined height due to the air injected into the air tube pads and apply uniform pressure to the chest and back of the wearer; and a connecting portion configured to couple the front portion and the rear portion to each other and allow a size of the vest outer skin to be adjusted according to a change in a size of the wearer's upper body.

The means for achieving the objectives of the present disclosure are not limited to those mentioned above, and other unmentioned means for achieving the objectives should be clearly understood by those of ordinary skill in the art to which the present disclosure pertains from the present specification and the accompanying drawings.

Advantageous Effects

According to the present disclosure, in wearing a compression vest for a child with a Autism Spectrum Disorder, there are advantageous effects that a sharp increase of air pressure due to air injection is prevented and the compression vest is allowed to be worn safely.

Also, according to the present disclosure, there is an advantageous effect that a therapeutic effect can be increased by adjusting an amount of air injected into air tube pads and an air pressure of the air tube pads according to preferences of a child with a Autism Spectrum Disorder.

Also, according to the present disclosure, by forming a linear adhesive portion and a circular adhesive portion on the air tube pads so that, when air is injected into the air tube pads, the air tube pads inflate evenly throughout at a predetermined height and apply uniform pressure to the chest and back of the wearer, there is an advantageous effect that a healing effect is increased due to giving a sense of stability to a child with a Autism Spectrum Disorder by letting the child feel as if his or her upper body is being warmly embraced.

Also, according to the present disclosure, since the air tube pads that inflate due to air injected into the air tube pads are induced to inflate inward toward the wearer's body, and an inner portion of a vest outer skin is made of a stretchy material, there is an advantageous effect that pressurization efficiency is increased relative to the amount of injected air.

In addition, according to the present disclosure, there are advantageous effects that, by a connecting portion, a front portion and a rear portion constituting the vest outer skin are coupled to each other so that the size of the vest outer skin can be adjusted according to a change in the size of the wearer's upper body, and a degree of adhesion of the compression vest to the wearer's body can be adjusted in cooperation with the pressure of the injected air.

The advantageous effects of the present disclosure are not limited to those mentioned above, and other unmentioned advantageous effects should be clearly understood by those of ordinary skill in the art to which the present disclosure pertains from the present specification and the accompanying drawings.

BEST MODE OF THE INVENTION

One embodiment of the present application provides a compression vest for a child with a Autism Spectrum Disorder, the compression vest including: a vest outer skin that consists of a front portion, which is a portion near a chest of a wearer, and a rear portion, which is a portion near a back of the wearer; an air tube pad embedded in each of the front portion and the rear portion of the vest outer skin; a driving portion configured to inject air into the air tube pads by a controller configured to control the air injected into the air tube pads; a sensor portion configured to check a set pressure and pressure maintenance time of the injected air; circular adhesive portions and linear adhesive portions that are formed on the air tube pads so that the air tube pads inflate evenly throughout at a predetermined height due to the air injected into the air tube pads and apply uniform pressure to the chest and back of the wearer; and a connecting portion configured to couple the front portion and the rear portion to each other and allow a size of the vest outer skin to be adjusted according to a change in a size of the wearer's upper body.

Modes of the Invention

The present disclosure relates to a compression vest 100 for a child with a Autism Spectrum Disorder that, during therapeutic education for a child with a Autism Spectrum Disorder to overcome the disability, helps stabilize the child to allow efficient progress in the therapeutic education. The present disclosure is based on the Deep Touch Pressure (DTP) theory of behavioristic psychology that states that, when a child with a Autism Spectrum Disorder wears the compression vest 100 having a set air pressure and pressure is simultaneously applied to the child's chest and back which constitute the upper body, the child's parasympathetic nerves are stimulated, which gives a sense of stability to the child and heals the child's disability.

Figure 1:
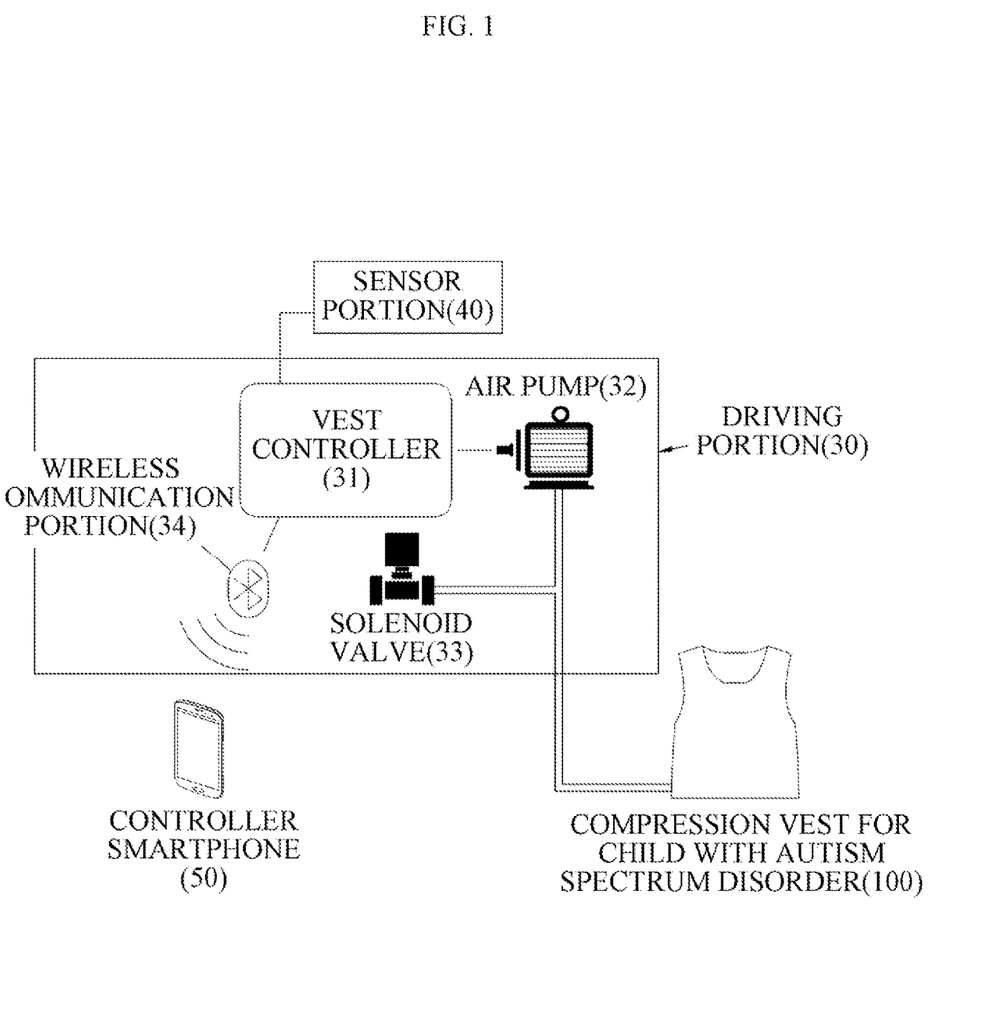
FIG. 1 is an operational state diagram according to the present disclosure.

Hereinafter, the present disclosure will be described in detail with reference to the accompanying drawings. FIG. 1 is an operational state diagram according to the present disclosure, and the present disclosure includes the compression vest 100 for a child with a Autism Spectrum Disorder into which air is injected, a driving portion 30 configured to control an air pressure of the compression vest 100, and a controller 50 allowing the driving portion 30 to be controlled using a smartphone which is a mobile phone. Also, although not illustrated in FIG. 1, a power supply formed of a battery configured to supply power necessary to operate elements such as the driving portion may be provided.

The driving portion 30 illustrated in FIG. 1 may include a vest controller 31, an air pump 32, a solenoid valve 33, and a wireless communication portion 34.

The vest controller 31 may control operations and functions of the elements provided in the driving portion. As an example, the vest controller 31 may control an air injecting operation of the air pump 32. As another example, the vest controller 31 may control an air ejecting operation of the solenoid valve. As still another example, the vest controller 31 may control communication between the wireless communication portion 34 and the controller 50 provided in a smartphone. As yet another example, the vest controller 31 may, based on data obtained from the controller control operations of elements connected to the vest controller 31. As yet another example, the vest controller 31 may, from a sensor portion 40, obtain air pressure information relating to pressure of air injected into the compression vest 100. As yet another example, the vest controller 31 may, based on the air pressure information obtained from the sensor portion, control at least one of the air pump and the solenoid valve.

The hardware configuration of the vest controller 31 may be provided using common, widely-used technology.

As an example, the vest controller 31 may be implemented using an electric unit or the like configured to serve as a microprocessor, a microcontroller, a digital signal processor (DSP), or a controller.

Also, according to implementation in terms of software, the vest controller 31 may be implemented together with a separate software module that performs at least one function or operation. Software code may be implemented by a software application written in any suitable programming language. Also, software code may be stored in a program-recordable storage medium and may be executed by the vest controller 31 or other elements.

The air pump 32 may serve to inject air into the compression vest for a child with a Autism Spectrum Disorder. In the configuration of FIG. 1, a motor pump is illustrated as being provided as the air pump that serves to inject air into the compression vest for a child with a Autism Spectrum Disorder. However, the element that serves to inject air into the compression vest for a child with a Autism Spectrum Disorder according to the present disclosure is not limited to a motor pump and may be implemented as various other pumps that can inject air into the compression vest for a child with a Autism Spectrum Disorder. However, hereinafter, for convenience of description, an example in which a motor pump is provided to inject air into the compression vest for a child with a Autism Spectrum Disorder will be described.

The solenoid valve 33 may serve to control a flow of a gas or fluid to eject the air injected into the compression vest for a child with a Autism Spectrum Disorder.

In the configuration of FIG. 1, a solenoid valve that serves to eject the air injected into the compression vest for a child with a Autism Spectrum Disorder is illustrated as being provided, but the present disclosure is not limited thereto, and various other valves may be provided to control a flow of a gas or fluid. However, hereinafter, for convenience of description, an example in which a solenoid valve is provided to eject the air injected into the compression vest for a child with a Autism Spectrum Disorder will be described.

The wireless communication portion 34 may be connected to the controller 50 by at least one communication method of wired communication and wireless communication. For example, the wireless communication may include mobile communication networks such as a Wi-Fi network, a third generation (3G) network, a long term evolution (LTE) network, a fifth generation (5G) network, and a long range (LoRa) network, a Wireless Access in Vehicular Environment (WAVE), beacons, ZigBee, BLUETOOTH® (i.e., short-range wireless technology), and BLUETOOTH® Low Energy (BLE).

The wired communication may include a twisted pair cable, a coaxial cable, a fiber optic cable, or the like and may also include communication connection through connection of simple communication lines or wires.

The wireless communication portion 34 may be connected to the vest controller 31. The wireless communication portion 34 may, from the controller 50, obtain a control signal for controlling an air pressure of the compression vest for a child with a Autism Spectrum Disorder and may provide the obtained control signal to the vest controller 31.

The controller 50 may be connected to the driving portion 30 by at least one communication method of the wireless communication and wired communication and may provide a control signal necessary for the operation of the driving portion 30 to the driving portion.

As an example, the controller 50 may be provided to be included in a mobile device such as a smartphone. Hereinafter, for convenience of description, an example in which the controller 50 is provided in a smartphone, which is a typical mobile device, will be described.

The controller 50 may, from a user, obtain control information relating to pressure of air to be provided to the compression vest 100 for a child with a Autism Spectrum Disorder through an application installed in a smartphone and may provide the obtained control information to the driving portion 30. As a more specific example, the controller 50 may provide the obtained control information to the vest controller 31 through the wireless communication portion 34.

The compression vest 100 for a child with a Autism Spectrum Disorder may, while worn by a user, simultaneously apply pressure to the user's chest and back which constitute the upper body, thus stimulating the user's parasympathetic nerves and giving a sense of stability to the user.

The compression vest 100 for a child with a Autism Spectrum Disorder may include a vest outer skin 10 and an air tube pad 20.

According to one embodiment of the present disclosure, information on pressure of air injected into the air tube pad 20 may be obtained through an application installed in a mobile terminal such as a smartphone. Also, according to one embodiment, the controller 50 may obtain an air pressure value input by a user through an input device provided in a smartphone, store the obtained air pressure value in a storage device provided in the smartphone, obtain a voice command from the user through a microphone provided in the smartphone, and control the air pressure based on the obtained voice command. Here, the controller 50 controlling the air pressure may include the controller 50 providing a control command obtained based on voice information input by the user to the vest controller 31 through a wireless communication module provided in the smartphone and the wireless communication portion 34 provided in the driving portion, and the vest controller 31 controlling at least one of the air pump 32 and the solenoid valve 33 to control the air pressure of the compression vest 100 for a child with a Autism Spectrum Disorder.

Air may be injected into the air tube pad 20 through the driving portion 30 driven by a control command of the controller 50. Also, the controller 50 may obtain information on a set pressure and pressure maintenance time of the injected air that is obtained through the sensor portion 40. Also, the controller 50 may, by providing a control signal necessary for the operation of the driving portion, operate in conjunction with the driving portion 30 and adjust the amount of injected air and the air pressure according to preferences of a child with a Autism Spectrum Disorder, who is the wearer, and to values necessary for therapy, and in this way, a therapeutic effect for the child with a Autism Spectrum Disorder may be increased.

Figure 2:
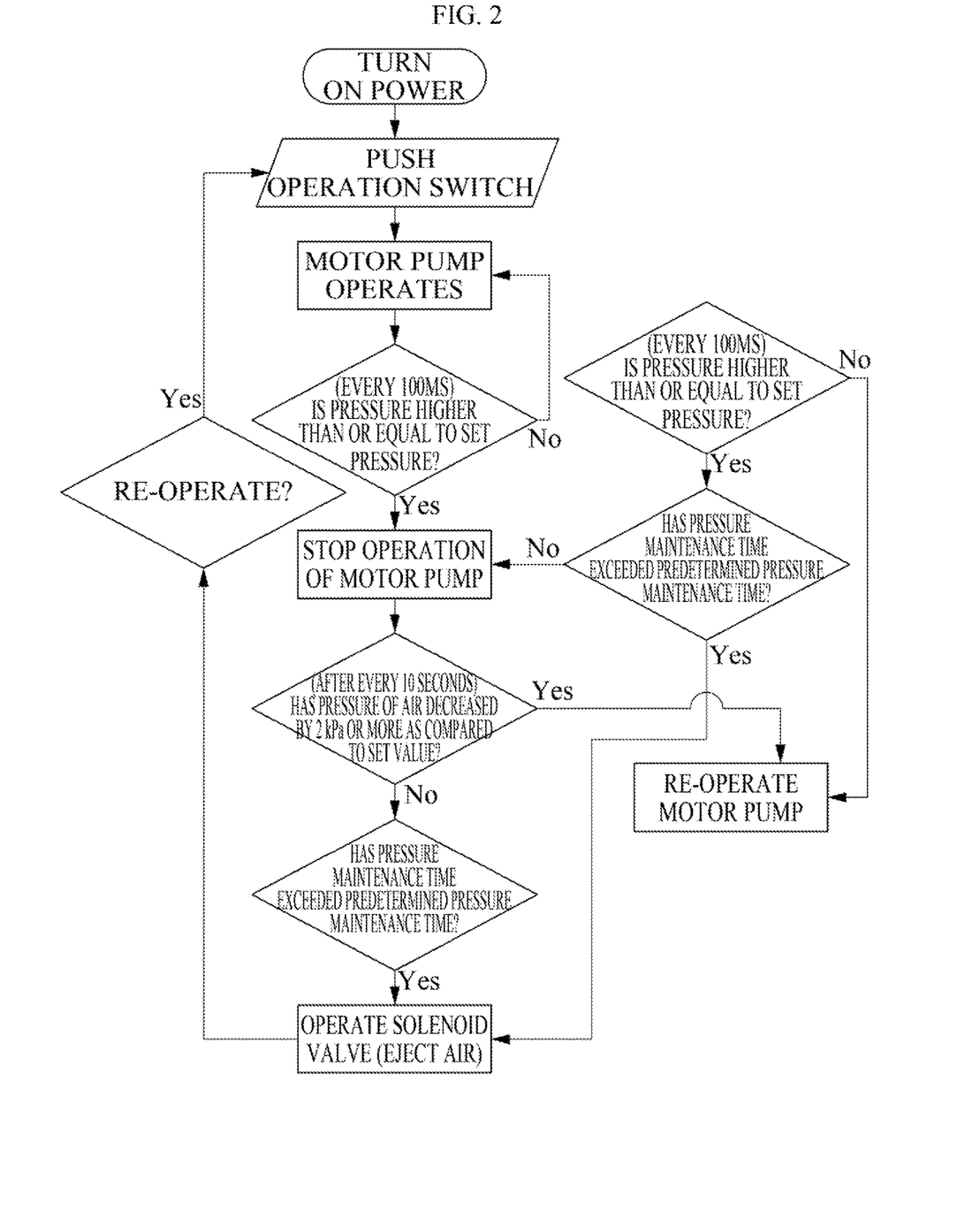
FIG. 2 is a flowchart of an algorithm of a driving portion according to the present disclosure.

FIG. 2 is a flowchart of an algorithm of the driving portion 30 according to the present disclosure. According to one embodiment, the driving portion 30 includes the air pump 32 configured to inject air into the air tube pad 20 and the solenoid valve 33 configured to eject the air to the outside. When a user operates a power button (not illustrated) to turn on the power and inputs an operation command through a push button of an operation switch, the air pump 32 provided in the driving portion 30 may be operated and inject air into the air tube pad 20.

More specifically, the vest controller 31 may obtain a command relating to air injection through a separate input device or the controller 50 and may, based on the obtained air injection command, control the air pump 32 to inject air into the air tube pad 20.

In order to prevent a sharp increase in the amount of injected air, the vest controller 31 may preset a predetermined set pressure of air and determine whether the pressure of the injected air is the set pressure or higher. Also, in a case in which the pressure of the injected air and/or an air pressure inside the compression vest 100 for a child with a Autism Spectrum Disorder are higher than or equal to a predetermined pressure, the vest controller 31 may control the air pump 32 to stop injecting air. Here, the vest controller 31 may, based on information obtained from the sensor portion 40, determine whether the pressure of the injected air and/or the air pressure inside the compression vest 100 for a child with a Autism Spectrum Disorder are higher than or equal to the predetermined pressure. The vest controller 31 may, at predetermined time periods, determine whether the air pressure inside the compression vest 100 for a child with a Autism Spectrum Disorder has dropped to a predetermined pressure or lower. Also, in a case in which the air pressure inside the compression vest 100 for a child with a Autism Spectrum Disorder has dropped to the predetermined pressure or lower, the vest controller 31 may control the air pump 32 to inject air into the compression vest 100 for a child with a Autism Spectrum Disorder. For example, after every 10 seconds which is a set pressure maintenance time, the vest controller 31 may cause the air pump 32 to re-operate in a case in which the pressure of the injected air has decreased by 2 kPa (Pascal) or more as compared to a set pressure value.

Also, in a case in which the pressure of the injected air and/or an air pressure inside the compression vest 100 for a child with a Autism Spectrum Disorder do not drop to the predetermined pressure or lower, when, based on a pre-identified pressure maintenance time, the pressure maintenance time exceeds a predetermined pressure maintenance time, the solenoid valve 33 may be operated to eject air from inside the air tube pad 20 provided in the compression vest 100 for a child with a Autism Spectrum Disorder, and whether to re-operate the driving portion 30 may be determined. The flowchart of the algorithm of the driving portion 30 that is shown in FIG. 2 is for, in wearing the compression vest for a child with a Autism Spectrum Disorder which is the present disclosure, preventing a sharp increase of air pressure due to air injection and allowing the compression vest to be worn safely.

FIGS. 3A to 3C are state views illustrating a vest outer skin and a front portion and a rear portion into which the vest outer skin is separated according to the present disclosure, and FIGS. 4A to 4C are state views illustrating a vest outer skin and a front portion and a rear portion into which the vest outer skin is separated according to another embodiment of the present disclosure.

FIG. 3A shows a vest outer skin 10 in which a front portion 11 and a rear portion 12 are coupled and integrally formed by a connecting portion 60, FIG. 3B shows the front portion 11 of the vest outer skin 10 that is near a chest of a wearer, and FIG. 3C shows the rear portion 12 of the vest outer skin 10 that is near a back of the wearer. In the front portion 11 which is the portion near the chest and the rear portion 12 which is the portion near the back, the connecting portion 60 is formed at portions that hang over the shoulders and portions that wrap around the waist, and as the front portion 11 and the rear portion 12 are coupled by the connecting portion 60, a single vest outer skin 10 is formed. In addition to coupling the front portion 11 and the rear portion 12 to each other so that the size of the vest outer skin 10 can be adjusted according to a change in the size of the wearer's upper body, the connecting portion provides a function that allows a degree of adhesion of the compression vest to the wearer's body to be adjusted in cooperation with the pressure of the injected air. A hook-and-loop fastener or the like which is easy to connect and separate may be provided as the connecting portion 60 according to one embodiment of the present disclosure, and an adjustable strap, an adjustable buckle, or the like may be provided as the connecting portion 60 according to implementation methods.

Figure 3:
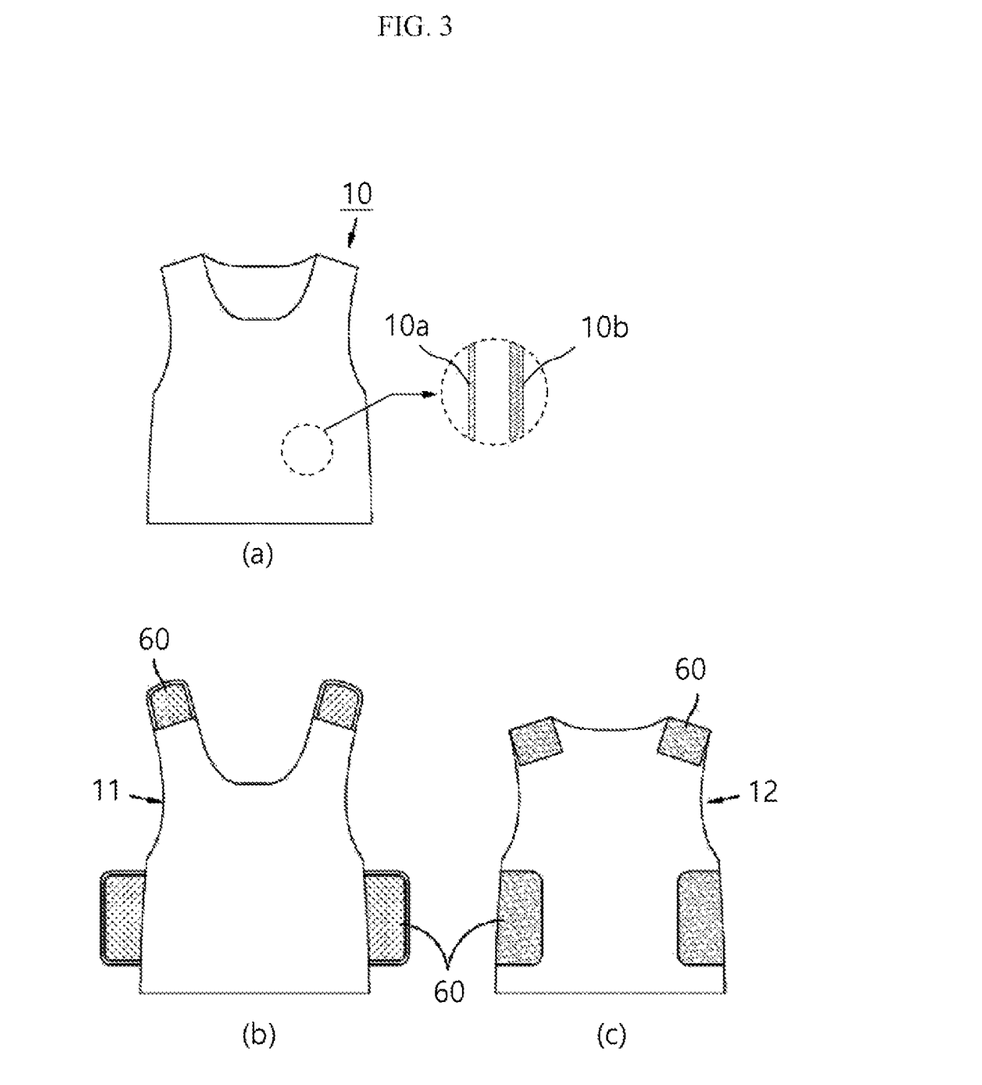
FIGS. 3A to 3C are state views illustrating a vest outer skin and a front portion and a rear portion into which the vest outer skin is separated according to the present disclosure.
Figure 4:
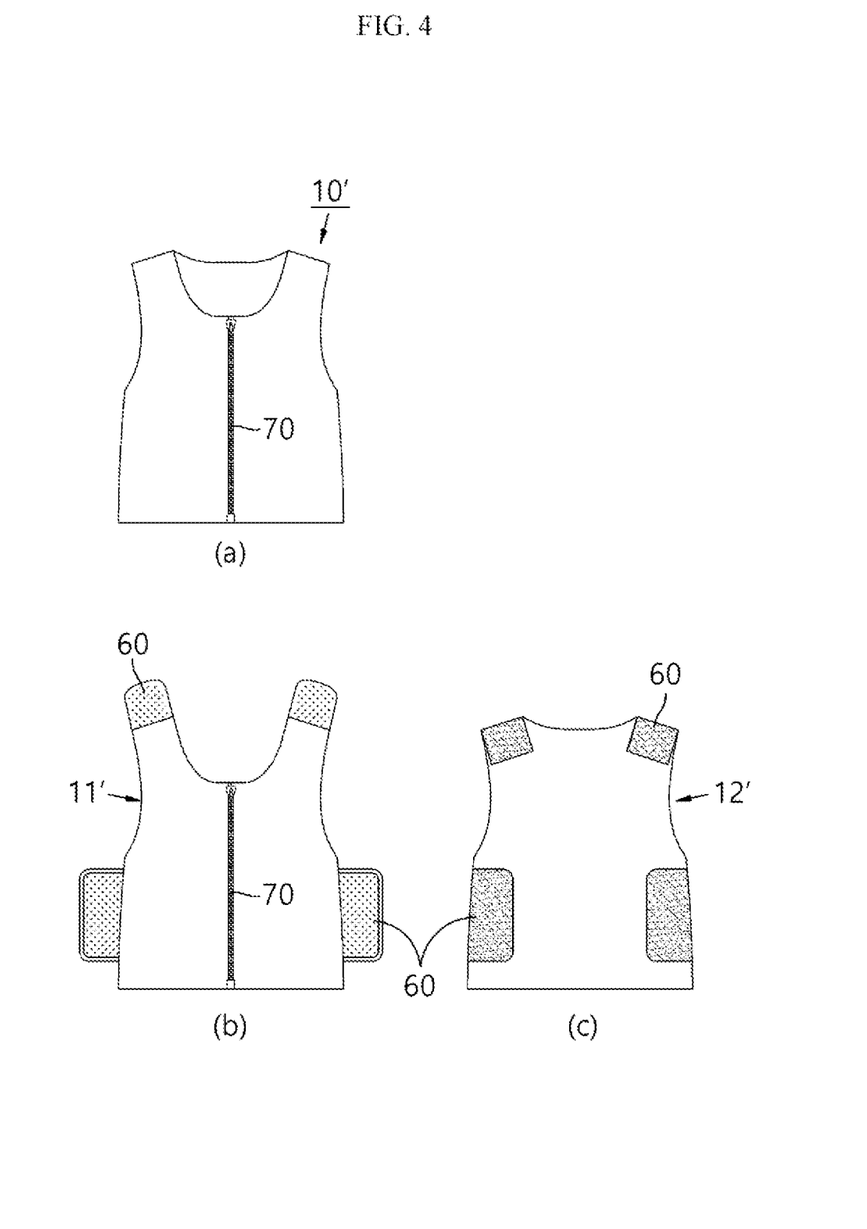
FIGS. 4A to 4C are state views illustrating a vest outer skin and a front portion and a rear portion into which the vest outer skin is separated according to another embodiment of the present disclosure.

The vest outer skin 10 according to the present disclosure has been described above as having a form in which the front and rear thereof are separately formed and coupled to each other through the connecting portion 60. However, the vest outer skin 10 according to the present disclosure is not limited to the form described above with reference to FIG. 3 and may, according to embodiments, be provided to have a form in which the front and rear thereof are coupled to each other without a separate connecting portion 60 being provided.

Referring to FIG. 3A, the vest outer skin 10 according to one embodiment may be provided to consist of two layers, an inner portion 10a and an outer portion 10b. Also, in more detail, the air tube pad 20 may include a front air tube pad 21 and a rear air tube pad 22. According to one embodiment, the front air tube pad 21 embedded in the front portion 11 and the rear air tube pad 22 embedded in the rear portion 12 may be provided between the inner portion 10a and the outer portion 10b.

The case in which the vest outer skin 10 is provided to consist of the two layers, the inner portion 10a and the outer portion 10b, and the air tube pad 20 is provided therebetween has been described above, but the present disclosure is not limited thereto, and according to embodiments, the vest outer skin 10 may be provided to consist of a single layer, and the air tube pad 20 may be provided to be coupled or attached to an inner side of the vest outer skin 10. As a more specific example, the front air tube pad 21 may be provided to be coupled or attached to an inner side of the front portion of the vest outer skin 10, and the rear air tube pad 22 may be provided to be coupled or attached to an inner side of the rear portion of the vest outer skin 10.

The inner portion 10a and the outer portion 10b of the vest outer skin 10 according to one embodiment may be provided to have different stretchability.

For example, the inner portion 10a of the vest outer skin 10 may be made of a relatively stretchier material as compared to the outer portion 10b of the vest outer skin, and the outer portion 10b of the vest outer skin may be made of a relatively less stretchy material as compared to the inner portion 10a of the vest outer skin 10. Since the inner portion 10a and the outer portion 10b of the vest outer skin 10 according to one embodiment are provided to have different stretchability, the air tube pad 20 embedded in the vest outer skin 10 may, while inflating due to injection of air thereinto, be naturally directed inward due to the inner portion 10a which is stretchy and the outer portion 10b which is non-stretchy, and in this way, pressurization efficiency can be increased relative to the amount of injected air.

Also, according to one embodiment, an additional accessory, such as a pouch for carrying a manual pump 70 or the like, may be provided for the vest outer skin 10.

Hereinafter, a vest outer skin 10 according to another embodiment of the present disclosure will be described with reference to FIGS. 4A to 4C. The vest outer skin 10 according to another embodiment which will be described below is formed by adding a zipper 70 to the configuration of the vest outer skin 10 according to one embodiment which has been described above with reference to FIG. 3. Descriptions of elements identical to those of the vest outer skin 10 according to one embodiment which has been described above with reference to FIG. 3 will be omitted.

Figure 6:
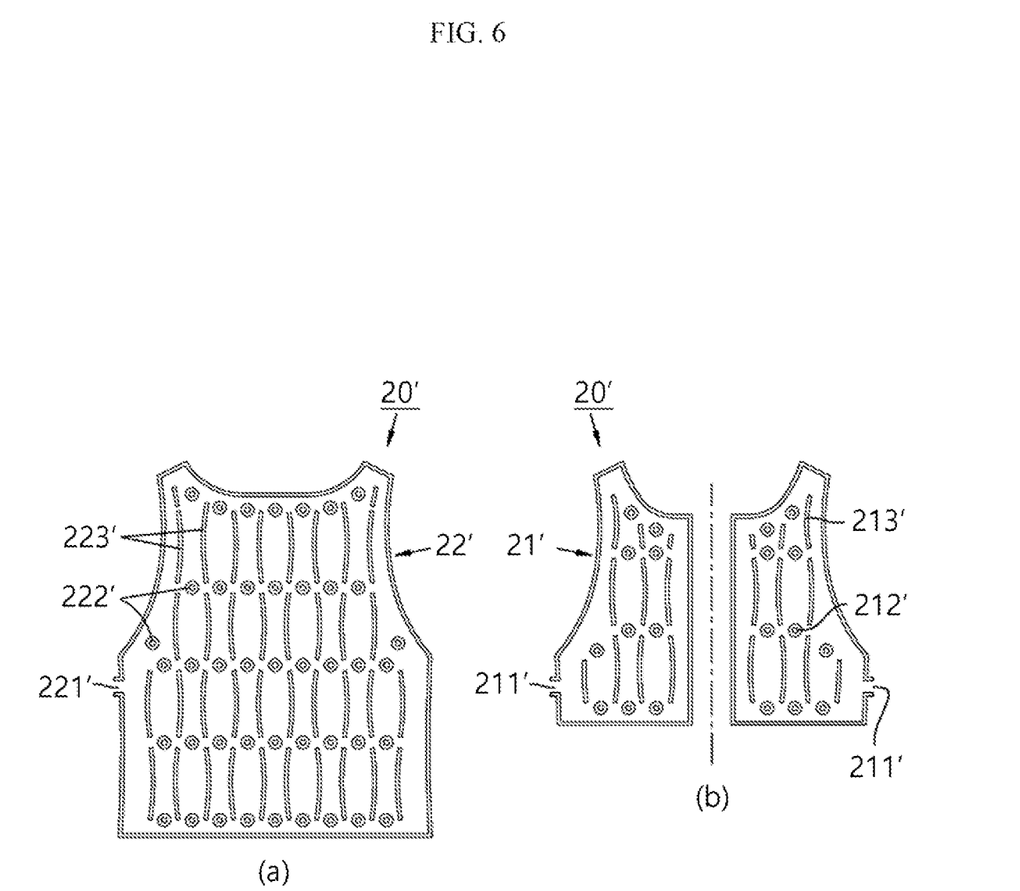
FIGS. 6A and 6B are cross-sectional views showing inner states of front and rear air tube pads embedded in a front portion and a rear portion of a vest outer skin according to another embodiment of the present disclosure.

In the vest outer skin 10 according to another embodiment of the present disclosure, the zipper 70 may be provided on a front portion 11', and the front portion 11' may be separated into two pieces by a coupling or separating operation of the zipper 70. Also, although not illustrated in FIG. 4, since the front portion 11' is enhanced to be separable, a front air tube pad 21' separated into two pieces may be provided as shown in FIG. 6.

Also, although an example in which the zipper 70 is added has been described above for convenience of description, the present disclosure is not limited thereto, and according to provision forms, an adjustable strap, an adjustable buckle, a button, or the like may be provided.

FIGS. 5A and 5B are views showing cross-sectional views of inner states of air tube pads embedded in a front portion and a rear portion of a vest outer skin according to the present disclosure. Also, FIGS. 6A and 6B relate to cross-sectional views of inner states of air tube pads embedded in the front portion and a rear portion of the vest outer skin 10 according to another embodiment of the present disclosure. FIG. 5A shows the rear air tube pad 22 of the air tube pad 20 of the present disclosure that is embedded in the rear portion 12. According to one embodiment, the rear air tube pad 22 may be provided to be embedded in or coupled to the rear portion 12 illustrated in FIG. 3C that forms the vest outer skin 10. Also, the front air tube pad 21 illustrated in FIG. 5B may be provided to be embedded in or coupled to the front portion 11 illustrated in FIG. 3B.

According to one embodiment, the front air tube pad 21 and the rear air tube pad 22 may include circular adhesive portions 212 and 222 and linear adhesive portions 213 and 223 so that the air tube pad 20 inflates evenly at a predetermined height throughout the portion near the wearer's chest and the portion near the wearer's back and thoroughly applies uniform pressure to the wearer's chest and back.

That is, the circular adhesive portions 212 and 222 of the air tube pad 20 may be formed by dot adhesion, and the linear adhesive portions 213 and 223 may be formed to have a predetermined length and formed by line adhesion. Also, the circular adhesive portions 212 and 222 may be disposed between ends of the linear adhesive portions 213 and 223 to form a path for injected air, and unit modules formed of the circular adhesive portions 212 and 222 and the linear adhesive portions 213 and 223 may be formed to be continuously connected on upper, lower, left, and right portions of the air tube pad 20.

Figure 5:
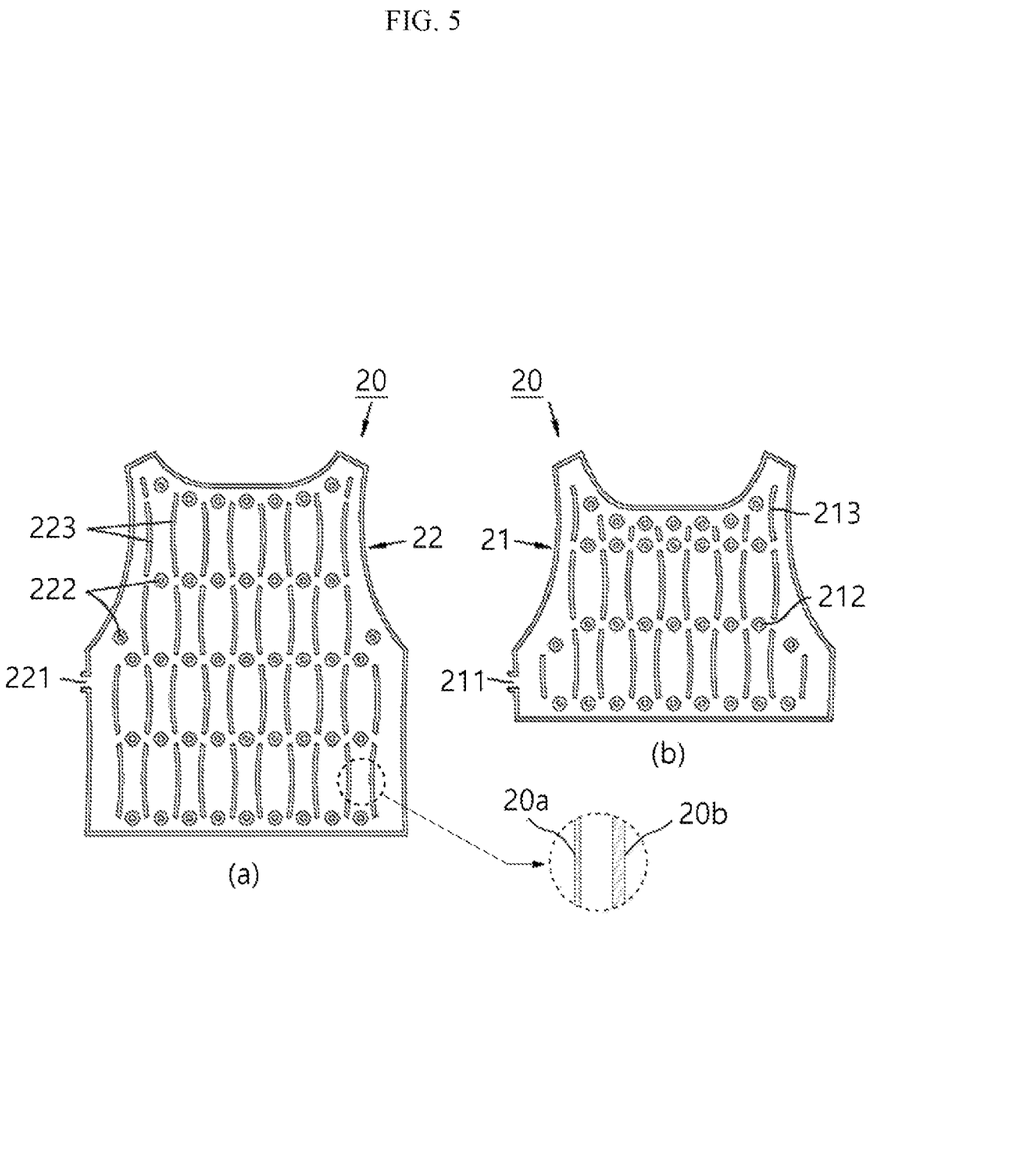
FIGS. 5A and 5B are cross-sectional views showing inner states of front and rear air tube pads embedded in a front portion and a rear portion of a vest outer skin according to the present disclosure.

For example, as illustrated in FIG. 5, the linear adhesive portions 213 and 223 may be provided to be formed by being adhered in a direction from an upper end toward a lower end at positions parallel to each other, and in this way, an air path formed by the linear adhesive portions 213 and 223 may be provided. Also, as illustrated in FIG. 5, the circular adhesive portions 212 and 222 may be provided at both ends of the air path formed by the linear adhesive portions 213 and 223.

The linear adhesive portions 213 and 223 according to one embodiment may be formed in a direction from an upper end of the air tube pad 20 toward a lower end thereof as illustrated in FIG. 5, but the present disclosure is not limited thereto, and according to embodiments, the linear adhesive portions 213 and 223 may be provided in the form of diagonal lines in a direction from an upper end of one side of the air tube pad 20 toward a lower end of the other side of the air tube pad 20, and in another example, the linear adhesive portions 213 and 223 may be provided in a direction from a left side of the air tube pad 20 toward a right side thereof.

Also, the linear adhesive portions 213 and 223 according to one embodiment may be provided in various forms in consideration of the body types of users. For example, an area in which the linear adhesive portions 213 and 223 are bonded, a width between the linear adhesive portions 213 and 223, a length of the linear adhesive portions 213 and 223, and the like may be differently provided according to the body shapes of users.

Also, regarding the linear adhesive portions 213 and 223 according to one embodiment, an area in which the linear adhesive portions 213 and 223 are bonded, a width between the linear adhesive portions 213 and 223, a length of the linear adhesive portions 213 and 223, and the like may be differently provided in consideration of the degree of pressure that should be applied to each body part of users.

For example, an interval between the linear adhesive portions 213 and 223 provided on the upper portion of the air tube pad 20 may be different from an interval between the linear adhesive portions 213 and 223 provided on the lower portion of the air tube pad 20. As a more specific example, the interval between the linear adhesive portions 213 and 223 provided on the upper portion of the air tube pad 20 may be provided to be relatively larger than the interval between the linear adhesive portions 213 and 223 provided on the lower portion of the air tube pad 20.

As another specific example, the interval between the linear adhesive portions 213 and 223 provided on the upper portion of the air tube pad 20 may be provided to be relatively smaller than the interval between the linear adhesive portions 213 and 223 provided on the lower portion of the air tube pad 20.

As another example, a length of the linear adhesive portions 213 and 223 provided on the upper portion of the air tube pad 20 may be different from a length of the linear adhesive portions 213 and 223 provided on the lower portion of the air tube pad 20. As a more specific example, the length of the linear adhesive portions 213 and 223 provided on the upper portion of the air tube pad 20 may be provided to be relatively longer than the length of the linear adhesive portions 213 and 223 provided on the lower portion of the air tube pad 20.

As another specific example, the length of the linear adhesive portions 213 and 223 provided on the upper portion of the air tube pad 20 may be provided to be relatively shorter than the length of the linear adhesive portions 213 and 223 provided on the lower portion of the air tube pad 20.

Like various forms of the linear adhesive portions 213 and 223 described above, the circular adhesive portions 212 and 222 may be provided in different sizes according to the body shapes of users and the degree of pressure that should be applied to users. For example, a size of the circular adhesive portions 212 and 222 provided on the upper portion of the air tube pad 20 and a size of the circular adhesive portions 212 and 222 provided on the lower portion of the air tube pad 20 may be different from each other.

Also, the size of the circular adhesive portions 212 and 222 may be provided to be proportional to the interval between the linear adhesive portions 213 and 223.

As an example, when two linear adhesive portions 213 and 223 are provided at left and right sides of a single adhesive portion unit module, and the circular adhesive portions 212 and 222 are provided at both ends of an air path formed by the two linear adhesive portions 213 and 223, a size of the circular adhesive portions 212 and 222 provided in a unit module in which an interval between the linear adhesive portions 213 and 223 is 2 cm may be provided to be larger than a size of the circular adhesive portions 212 and 222 provided in a unit module in which an interval between the linear adhesive portions 213 and 223 is 1 cm.

According to one embodiment of the present disclosure, by the above shapes, the unit modules in which the circular adhesive portions 212 and 222 are disposed between the ends of the linear adhesive portions 213 and 223, which are formed to have a predetermined length in the air tube pad 20, may be formed to be continuously connected on the upper, lower, left, and right portions of the air tube pad 20, and thus an effect that injected air is prevented for a long period of time from escaping to the outside may occur. In particular, the linear adhesive portions 213 and 223 may, instead of being formed in a straight shape, have a convex central portion or be formed with a certain concave line of curvature, and the linear adhesive portions 213 and 223 having a convex central portion or formed with a certain concave line of curvature may be provided to be formed symmetrically and continuously on the air tube pad. Also, due to such shapes, the air tube pad 20 into which air is injected inflates evenly throughout and applies uniform pressure to the wearer, thus letting the wearer feel as if his or her upper body is being warmly embraced. Accordingly, the air tube pad 20 in which the circular adhesive portions 212 and 222 and the linear adhesive portions 213 and 223 are formed inflates evenly throughout at a predetermined height due to the air injected thereinto and applies uniform pressure to the chest and back of the wearer, and thus parasympathetic nerves of a child with a Autism Spectrum Disorder may be stimulated and a sense of stability can be given to the child by letting the child feel as if his or her back and chest, which constitute the upper body, are being warmly embraced. As a result, a healing effect can be increased. A sense or pressure felt by the wearer may be the gentlest in a case in which the overall thickness of the air tube pad 20 when the air tube pad 20 inflates evenly is in a range of about 15 to 20 mm.

Also, the air tube pad 20 may be made of a nontoxic, eco-friendly material, such as thermoplastic urethane, having a certain thickness. Also, of course, the air tube pad 20 may also be formed of an inner skin 20a and an outer skin 20b to accommodate air injected thereinto, and in order to induce the air tube pad that inflates due to the air injected thereinto to inflate inward toward the wearer's body, primarily, a thickness the outer skin 20b of the air tube pad 20 may be formed to be thicker than a thickness of the inner skin 20a of the air tube pad 20. In this way, pressure of the air injected into the air tube pad 20 is mostly directed inward, and thus pressurization efficiency is increased relative to the amount of injected air. Also, since the inner portion 10a of the vest outer skin 10 is made of a stretchy material and the outer portion of the vest outer skin 10 is made of a non-stretchy material as described above, there is a secondary effect that the pressurization efficiency is further increased while not inhibiting the inward inflation of the air tube pad 20 embedded in the vest outer skin 10.

That is, in order to induce the air tube pad 20 that inflates due to air injected thereinto to inflate inward toward the wearer's body, primarily, the thickness of the outer skin 20b of the air tube pad 20 is formed thicker than the thickness of the inner skin 20a of the air tube pad 20, and secondarily, the inner portion 10a of the vest outer skin 10 is made of a stretchy material and the outer portion 10b of the vest outer skin 10 is made of a non-stretchy material to increase efficiency of pressurization by the air tube pad 20.

Also, the circular adhesive portions 212 and 222 formed in small circles by dot adhesion on the air tube pad 20 and the linear adhesive portions 213 and 223 formed in predetermined lengths by line adhesion on the air tube pad 20 may be formed by being pressed and compressed using a prefabricated high-frequency fusion device having a certain temperature in order to form the circular adhesive portions 212 and 222 and the linear adhesive portions 213 and 223 while the inner skin 20a and the outer skin 20b of the air tube pad 20 face each other. A common, widely-applied compression device may be used for the high-frequency fusion device or compression method.

Since the unit modules including the circular adhesive portions 212 and 222 and the linear adhesive portions 213 and 223 are continuously connected, and the air tube pad 20 inflates thoroughly at a uniform height due to air injected thereinto, when the compression vest of the present disclosure is worn, not only a degree of freedom of movement of the wearer's upper body is increased, but also, even in a case in which the air tube pad 20, which is formed by continuously connecting the unit modules including the circular adhesive portions 212 and 222 and the linear adhesive portions 213 and 223, is deflated and folded for storage, the air tube pad 20 is folded with the circular adhesive portions 212 and 222 and other adjacent, continuous circular adhesive portions 212 and 222 as a folding line, and in this way, there are effects that it is easy to fold the air tube pad 20, and damage to the air tube pad 20 due to folding is prevented even when the air tube pad 20 is stored for a long period of time.

FIGS. 6A and 6B is mostly the same as the air tube pad 20 of FIGS. 5A and 5B and is different therefrom in that the front portion 11' forming the vest outer skin 10' is separated by the zipper 70 disposed at the center. The front air tube pad 21' embedded in the separated front portion 11' is the only difference, and formation of circular adhesive portions 212' and 222' and linear adhesive portions 213' and 223', which are formed in the air tube pad 20', is the same as that described above.

Figure 7:
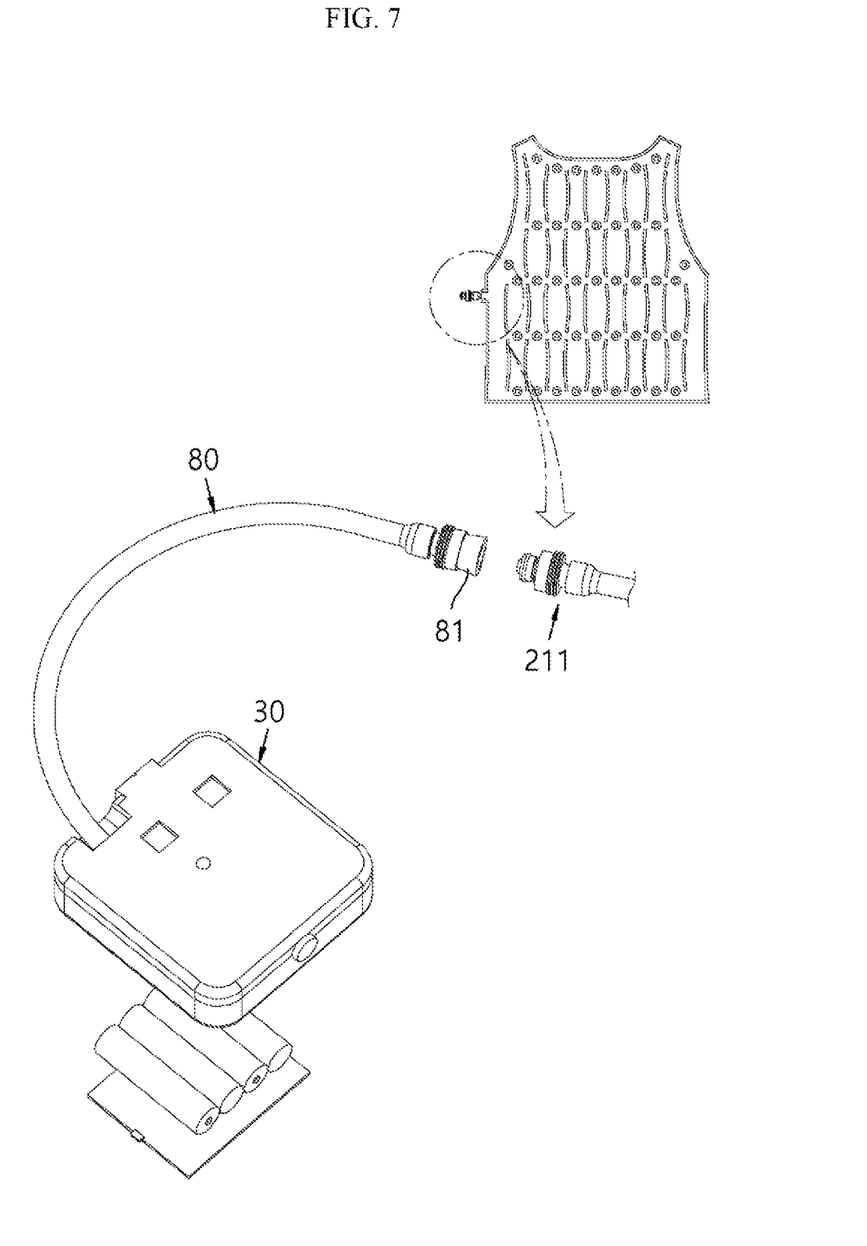
FIG. 7 is a state view illustrating coupling between a driving portion and a rear air tube pad according to the present disclosure.

FIG. 7 is a state view illustrating coupling between a driving portion and a rear air tube pad according to the present disclosure. A connector 81 of an injection pipe connected to the driving portion 30 is connected to an air injection port 211 of the air tube pad 20 and then air is injected. The air injection port 211 may be formed at one side of the air tube pads 20 and 20' or may be formed at both sides thereof as necessary.

More specifically, the injection pipe 80 may be connected to the air pump 32 provided in the driving portion 30. Also, the connector 81 may be provided at one end of the injection pipe 80, and the connector 81 may be connected to the air injection port 211 provided in the air tube pad 20. By such a connection relationship, air injected from the air pump 32 may be injected into the air tube pad 20 through the injection pipe 80.

According to another embodiment of the present disclosure, a manual pump may be provided in place of the driving portion 30.

Figure 8:
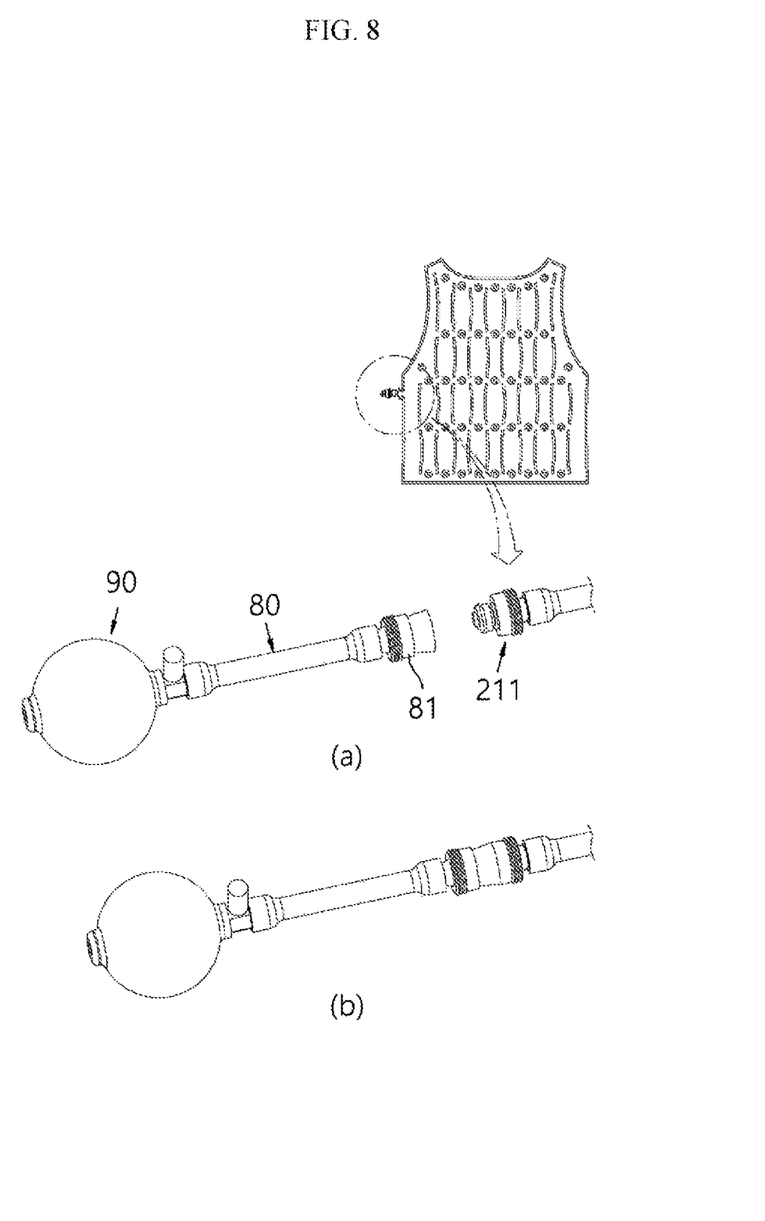
FIGS. 8A and 8B are state views illustrating separation and coupling between a rear air tube pad and a manual pump according to the present disclosure.

FIGS. 8A and 8B are state views illustrating separation and coupling between an air tube pad and a manual pump according to the present disclosure. A connector 81 of an injection pipe 80 of the manual pump 90 may be separated from and coupled to the air injection port 211 formed in the air tube pads 20 and 20'.

Figure 9:
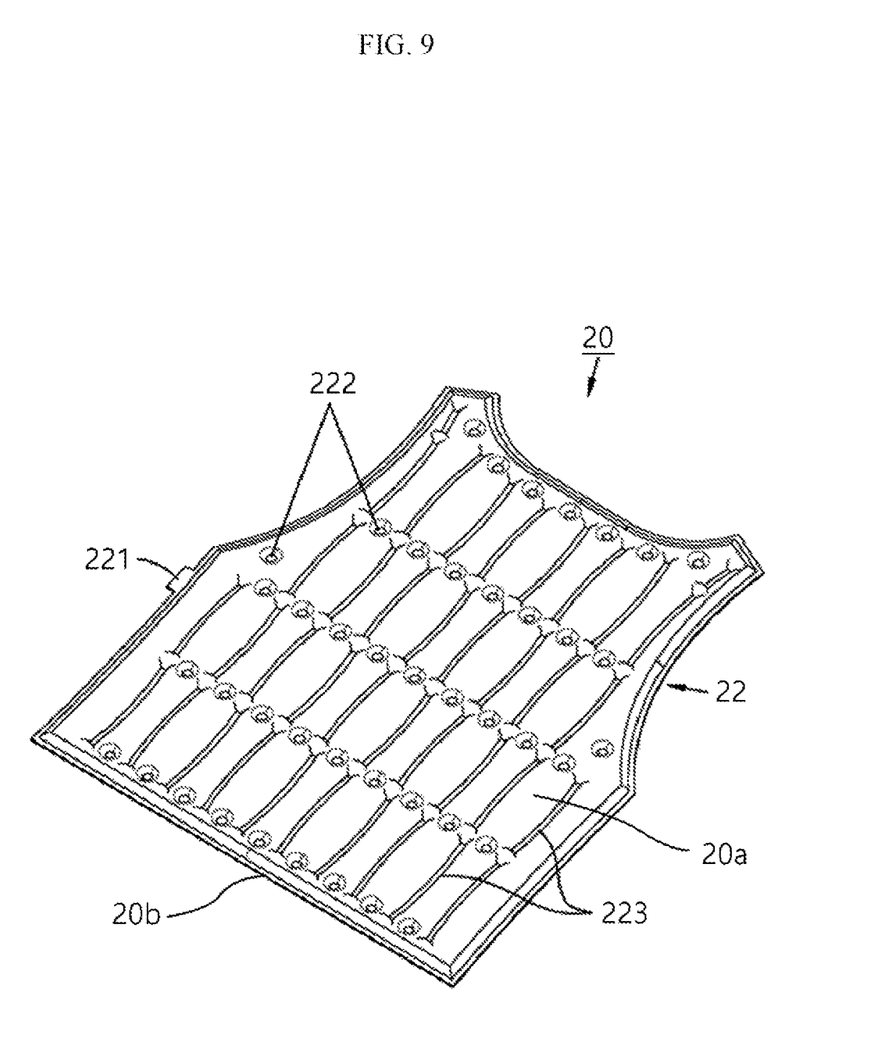
FIG. 9 is a perspective view of an air tube pad into which air is injected according to the present disclosure.

FIG. 9 is a perspective view of an air tube pad into which air is injected according to the present disclosure and shows a state in which the air tube pad 20 having the circular adhesive portion 222 and the linear adhesive portion 213 formed thereon is inflated evenly throughout due to air injected into the air tube pad 20.

The present disclosure has been described above using only some embodiments and the drawings, and the terms used in the present specification and the claims should be, instead of being construed as being limited to ordinary or dictionary meanings, construed as having the meaning and concept consistent with the technical spirit of the present disclosure. Accordingly, configurations described or illustrated in the embodiments or the drawings herein are only some embodiments of the present disclosure and do not represent the entire technical spirit of the present disclosure. Therefore, it should be understood that various equivalents and modifications may be present within the scope not departing from the claims of the present disclosure.

The invention claimed is:

1. A compression vest for a child with an autism spectrum disorder, the compression vest comprising:
    a vest outer skin including a front portion which is a portion configured to correspond to a chest of a user, and a rear portion which is a portion configured to correspond to a back of the user;
    an air tube pad embedded in each of the front portion and the rear portion of the vest outer skin;
    a driving portion configured to inject air into the air tube pads by a controller configured to control the air injected into the air tube pads;
    a sensor portion configured to check a set pressure and pressure maintenance time of the injected air;
    discrete circular adhesive portions and discrete linear adhesive portions that are formed on each of the air tube pads so that the air tube pads inflate evenly throughout at a predetermined height due to the air injected into the air tube pads and apply uniform pressure to the chest and back of the user; and
    a connecting portion configured to couple the front portion and the rear portion to each other and allow a size of the vest outer skin to be adjusted according to a change in a size of the user's upper body,
    wherein the circular adhesive portions formed on the air tube pads are formed by dot adhesion, the linear adhesive portions are formed to have a predetermined length and formed by line adhesion, and unit modules in which the circular adhesive portions are disposed between ends of the linear adhesive portions to form a path for the injected air and are formed to be continuously connected on upper, lower, left, and right portions of the air tube pads,
    wherein the linear adhesive portions include a first plurality of concave-shaped linear adhesive portions and a second plurality of convex-shaped linear adhesive portions,
        each of the first plurality of concave-shaped liner adhesive portions having a first concave curved shape with a first central portion, and
        each of the second plurality of convex-shaped liner adhesive portions having a second convex curved shape with a second central portion,
        wherein each of the first plurality of concave-shaped linear adhesive portions and each of the second plurality of convex-shaped linear adhesive portions are arranged alternately on the air tube pads,
    wherein the linear adhesive portions are formed symmetrically and continuously on the air tube pads.

2. The compression vest of claim 1, wherein, in order to induce the air tube pads that inflate due to the air injected thereinto to inflate inward toward the user's body, primarily, a thickness of an outer skin of the air tube pads is formed thicker than a thickness of an inner skin of the air tube pads, and secondarily, an inner portion of the vest outer skin is made of a stretchy material and an outer portion of the vest outer skin is made of a non-stretchy material, wherein the stretchy material is relatively stretchier than the non-stretchy material.

3. The compression vest of claim 1, wherein a front air tube pad embedded in the front portion of the vest outer skin is formed as one body or formed to be separated into two parts.

4. The compression vest of claim 1, wherein the driving portion includes an air pump configured to inject air into the air tube pads and a solenoid valve configured to eject the air to an outside.

5. The compression vest of claim 1, wherein air is able to be injected into the air tube pads using a manual pump.

6. The compression vest of claim 1, wherein the connecting portion is configured using a hook-and-loop fastener.

\* \* \* \* \*